(12) United States Patent
Nguyen et al.

(10) Patent No.: US 7,439,074 B2
(45) Date of Patent: Oct. 21, 2008

(54) METHOD OF ANALYSIS OF ALCOHOL BY MASS SPECTROMETRY

(76) Inventors: Hoa Duc Nguyen, 7735 E. Fieldcrest La., Orange, CA (US) 92869; Trinh Duc Nguyen, 2077 S. Sprague La., #1, Anaheim, CA (US) 92802; Duc Tien Nguyen, 14701 Bowling Green, Westminster, CA (US) 92683

( * ) Notice: Subject to any disclaimer, the term of this patent is extended or adjusted under 35 U.S.C. 154(b) by 922 days.

(21) Appl. No.: 10/675,765

(22) Filed: Sep. 30, 2003

(65) Prior Publication Data

US 2005/0070024 A1   Mar. 31, 2005

(51) Int. Cl.
  *G01N 24/00* (2006.01)
  *G01N 33/14* (2006.01)
(52) U.S. Cl. .......................... 436/173; 436/24
(58) Field of Classification Search .............. None
  See application file for complete search history.

(56) References Cited

OTHER PUBLICATIONS

Johnson et al. "A rapid screening procedure for cholesterol and dehydrocholesterol by electrospray ionization tandem mass spectrometry", Journal of Lipid Research, 2001, v. 42, pp. 1699-1705.*

Esteban et al. "Stable Isotope Dilution Thermospray Liquid Chromatography/Mass Spectrometry Method for Determination of Sugars and Sugar Alcohols in Humans", Anal. Chem. 1987, v. 59, 1674-1677.*

Dufour et al. "Quantitative analysis of beer aromatic alcohols using stable isotope dilution assay", Journal of the American Society of Brewing Chemists, 2002, v. 60(2), 88-96.*

Pyon et al. "An isotope-dilution gas chromatography-mass spectrometry method for trace analysis of xylene metabolites in tissues", J. Anal. Toxicol., 1997, v. 21, pp. 363-368.*

Aubry et al. "Quantitative Determination of Potent Flavor Compounds in Burgundy Pinot Noir Wines Using a Stable Isotope Dilution Assay", J. Agric. Food Chem. 1997, v. 45, pp. 2120-2123.*

Woidich et al. "The Use of N-Alkylcarbamates in Sample Mapping of Terpene Alcohols", Mikrochim. Acta, [Wien] 1989, III, pp. 117-124.*

Quirke et al. "Electrospray tandem mass spectrometric study of ferrocene carbamate ester derivatives of saturated primary, secondary and tertiary alcohols", J. Mass Spectrom. 2001, v. 36, pp. 179-187.*

Quirke et al. "Ferrocene-Based Electroactive Derivatizing Reagents for the Rapid Selective Screening of Alcohols and Phenols in Natural Product Mixtures Using Electrospray-Tandem Mass Spectrometry", J. Nat. Prod. 2000, v. 63, pp. 230-237.*

* cited by examiner

*Primary Examiner*—Yelena G Gakh

(57) ABSTRACT

Method of identification and quantitative analysis of alcohol (s) in a sample by mass spectrometry using stable isotope labeled internal standard is provided. Said internal standard is prepared by reaction of an authentic sample of said alcohol with a stable isotope labeled reagent, and is added to a sample containing said alcohol. Said alcohol in said sample is then quantitatively converted to a chemical compound of identical structure, except the stable isotope atoms, as that of said internal standard using a non-labeled reagent. Said sample is then extracted and the extract is analyzed by mass spectrometry. Identification and quantification of said alcohol are made from a plot of ion ratio of said converted alcohol to said internal standard versus alcohol concentration.

18 Claims, No Drawings

METHOD OF ANALYSIS OF ALCOHOL BY MASS SPECTROMETRY

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

This invention pertains to methods of quantitative analysis of alcohols in a sample by isotope dilution mass spectrometry. The stable isotope labeled esters and carbamates are used as internal standards. The sample may be a biological fluid, such as serum, urine etc., or an aqueous sample such as an environmental or an agricultural sample.

While various methods of analysis such as immunoassays and chromatographic analysis—LC (liquid chromatography), GC (gas chromatography), and TLC (thin layer chromatography)—have been reported for identification and determination of levels of alcohols in analytical samples, the absolute and unequivocal identification and quantitative analysis of those compounds are combinations of chromatographic analysis and MS (mass spectrometry) such as GC-MS and LC-MS. The accuracy and precision of these methods are usually the highest when stable isotope analogs of the analytes are used as internal standards. The mass spectrometry method of analysis using stable isotope internal standards is commonly called isotope dilution mass spectrometry. This method takes advantage of the similar chemical and physical behaviors of analytes and their respective isotope labeled internal standards towards all phases of sample preparation and also towards instrument responses. It uses the mass differentiation between analytes and their respective internal standard in mass spectrometry for quantification. The requirement for this method of analysis is the availability of stable isotope labeled internal standards.

The commonly used stable isotope labeled internal standard of an analyte is a chemical compound that has the same chemical structure as that of the analyte except that one or more substituent atoms are stable isotopes. Four commonly used stable isotopes are deuterium, carbon-13, nitrogen-15, and oxygen-18. For every hydrogen atom that is replaced by a deuterium atom, the molecular weight of resulting chemical compound is increased by one mass unit. This is also true for replacing a carbon atom with a carbon-13 atom, or by replacing a nitrogen atom with a nitrogen-15 atom. In the case of replacing an oxygen atom with an oxygen-18 atom, the molecular increase is two mass units. Although the acceptable stable isotope labeled internal standard for isotope dilution mass spectrometry method is the one that is not contaminated with any of the unlabeled material, the ideal one should be the one with the highest isotopic purity and contains as many stable isotope atoms as possible. The ideal one, however, must not contain any labeled isotope that can be exchanged for the unlabeled isotope under particular sample preparation conditions.

These criteria of an ideal stable isotope labeled internal standard present a challenge for organic synthesis chemists who help the analytical chemists in the analysis. Most often the synthesis of stable isotope internal standards is not simply an isotope exchange reaction. Easily exchangeable atoms are usually avoided due to possible re-exchange during sample preparation steps. Organic chemists often have to carry out multi-step synthesis to make stable isotope labeled internal standards. Even though many stable isotope labeled reagents are commercially available, the choice of appropriate labeled reagent for chemical synthesis of stable isotope labeled internal standards is still very limited. The limited isotope labeled reagents and the multi-step synthesis contribute to the high cost of synthesis of stable isotope internal standards. Even if the analytical chemist who carries out the analysis can afford the cost of the synthesis, there is also a time factor that he or she has to consider before ordering the synthesis. Situations where organic chemists spent weeks and months on a synthesis project and came up with nothing at the end were common. This invention offers a solution for this problem.

The objective is a short and reliable method of preparing a stable isotope labeled internal standard that is suitable for the analysis of an analyte in question, but not the synthesis of the stable isotope labeled analyte. Within the context of the isotope dilution mass spectrometry method, both analyte and its internal standard have to have identical chemical structures, with the exception of the isotope atoms which provide the mass differentiation upon mass spectrometric analysis. Analytical chemists who uses GC-MS for their analysis often "derivatize" the analyte and its stable isotope labeled analyte (used as internal standard) into chemical compounds that can easily pass through the GC column or else provide better instrumental responses. The analysis becomes the analysis of the "derivatized" analyte and the "derivatized" internal standard, but still provides comparably accurate results of concentrations of the analyte itself. Examples of these analyses are found in cited references. Using similar reasoning, one can synthesize a stable isotope derivative of the analyte by reacting it with a stable isotope labeled reagent. The resulting isotope labeled chemical compound can be used as internal standard in the analysis of the analyte, providing that the analyte in the analyzed sample will be converted to a chemical compound of identical structure as that of the internal standard using a non-labeled reagent. There are 3 requirements for the usefulness of this method:

1. The analyte in the sample must be quantitatively converted to the compound of identical structure (except the labeled atoms) as that of the added isotope labeled internal standard using a non-labeled reagent.
2. Absolutely no conversion of the isotope labeled internal standard to the non-labeled compound because the conversion of the analyte happens in the sample in the presence of the added isotope labeled internal standard.
3. The conversion of the analyte into the compound of identical structure as that of the added isotope labeled internal standard has to be accomplished before any isolation method i.e. extraction, is performed.

The first two requirements relate to the chemistry of the analyte in question. The efficiency of a chosen chemical reaction depends on the type of reaction which, in turn, depends on the type of functional groups of the analyte. This invented method relates to the analysis of alcohols whose chemistry focus on the reactivity of the hydroxyl functional groups of the analytes.

Quantitative reactions of alcohols in aqueous samples are:
1. Conversion to an ester using an acid anhydride or an acid chloride.
2. Conversion to a carbamate using an isocyanate.

There are other reactions of alcohols that are very efficient, but the above conversion reactions are very efficient in aqueous environment and can be performed at room temperature and in a relatively short reaction time. These are necessary and practical features for routine analysis of alcohols in aqueous samples.

BRIEF SUMMARY OF THE INVENTION

The current invention provides for a method of identification and quantification of alcohol in a sample by isotope dilution mass spectrometry. The stable isotope labeled internal standard of said alcohol is synthesized beforehand by reacting a sample containing said analyzed alcohol with a labeled reagent. Following this step, said stable isotope labeled internal standard is then added to a sample containing said analyzed alcohol. Said analyzed alcohol is then converted to a non-labeled analog of said labeled internal standard with identical chemical structure as said labeled internal standard except for the stable isotope atoms using a non-labeled reagent. Both said converted analyzed alcohol and said stable isotope labeled internal standard are then extracted and analyzed by mass spectrometry. Said stable isotope labeled internal standards provided in the current invention are labeled ester and carbamate analogs of said analyzed alcohol. The type of labeled internal standard used will dictate said labeled reagents used for its synthesis as well as said non-labeled reagent used to convert the analyzed alcohol to the corresponding analog.

In comparison with the traditional method of isotope dilution mass spectrometric analysis of more than one alcohols, the invented method offers the following advantages:

1. The efficiency and simplicity of the above reactions makes possible the short, reliable, and quick synthesis of individual stable isotope labeled internal standards, whereas in the traditional method of analysis, stable isotope labeled internal standard of each alcohol has to be independently synthesized.
2. It is possible to quickly and efficiently synthesize a library of stable isotope internal standards for the analysis of an entire library of alcohols using these reactions and only one commercially available stable isotope labeled reagent.
3. Because the synthesis of stable isotope labeled internal standard in this invented method is usually a one-step synthesis, the entire process of synthesis and sample preparation can be performed in an automated fashion. The internal standard is prepared in one step, excess isotope reagent is then destroyed, and the prepared internal standard can be added directly to the samples without purification. The non-labeled reagent is added and the sample is ready for extraction shortly thereafter.

These attractive features make the method suitable for high throughput analysis of alcohols by isotope dilution mass spectrometry.

DETAILED DESCRIPTION OF THE INVENTION

The current invention provides for a method of identification and quantification of alcohol(s) in a sample by mass spectrometry. Said alcohol(s) has the following formulas $R_1OH$, $R_1CH_2OH$, $R_1R_2CHOH$, $R_1R_2R_3COH$ wherein $R_1$, $R_2$, and $R_3$ are alkyl, aryl, and heteroatom containing cyclic or non-cyclic groups. The current method comprises, as an intergral part of the analysis of said alcohol(s), the following steps:

1. Synthesizing labeled ester internal standard(s) by reacting an authentic sample of said alcohol(s) with a stable isotope labeled reagent to form said ester internal standard(s) of the general formulas $R_1OCOR_4$ or $R_1CH_2OCOR_4$ or $R_1R_2CHOCOR_4$ or $R_1R_2R_3COCOR_4$, wherein $R_4$ is a stable isotope labeled alkyl or aryl group. Said $R_4$ stable isotope labeled alkyl or aryl group is selected from the group consisting of $CD_3$, $CD_2CD_3$ or $C_6D_5$. Said stable isotope labeled reagent is a labeled acid anhydride or an acid chloride selected from a group consisting of labeled acetic acid anhydride, labeled propionic acid anhydride and labeled benzoic acid anhydride or labeled acetyl chloride, labeled propionyl chloride, and labeled benzoyl chloride.
2. A known amount of said stable isotope labeled ester internal standard(s) was then added to said sample containing said alcohol(s) to be analyzed.
3. Said sample was then contacted with a non-labeled acid anhydride or an acid chloride selected from a group consisting of acetic acid anhydride, propionic acid anhydride and benzoic acid anhydride or acetyl chloride, propionyl chloride, and benzoyl chloride to quantitatively convert said alcohol(s) in said sample into said ester(s) of identical structure as that of said ester internal standard(s) except for the stable isotope atoms.
4. Appropriate extraction methods were then used to isolate said ester(s) and their corresponding ester internal standard (s) from said sample. Concentration of said ester(s) were determined and quantified by mass spectrometry and based on the ratio of said converted ester(s) and their corresponding ester internal standard(s).

In another aspect of the present invention, said labeled internal standard is a stable isotope labeled carbamate. In this embodiment, said stable isotope labeled carbamate(s) is synthesized by reacting an authentic sample of said alcohol(s) with a stable isotope labeled reagent to form said carbamate internal standard(s) having the following formula $R_1OCONR_4$ or $R_1CH_2OCONR_4$ or $R_1R_2CHOCONR_4$ or $R_1R_2R_3COCONR_4$ wherein $R_4$ is a stable isotope labeled alkyl or aryl group selected from the group consisting of $CD_3$, $CD_2CD_3$, $C_6D_5$. Said stable isotope labeled reagent is a labeled isocyanate selected from a group consisting of labeled methyl isocyanate, labeled ethyl isocyanate and labeled phenyl isocyanate. Also, in this embodiment, said analyzed alcohol(s) is converted to carbamate(s) of identical structure as that of said carbamate internal standard(s) except for the stable isotope atoms by contacting said sample with a non-labeled isocyanate selected from a group consisting of methyl isocyanate, ethyl isocyanate and phenyl isocyanate.

EXAMPLE

Analysis of Naltrexone in Human Plasma

Step 1: Preparation of Naltrexone Acetate Ester-d3.

A solution of 2.5 mg of Naltrexone in 0.5 ml aqueous sodium bicarbonate was treated with 5 equivalents of acetic anhydride-d6. The resulting solution was stirred for 2 hours then the aqueous phase was extracted with ethyl acetate-hexane mixture and the combined organic phases were dried with magnesium sulfate. The filtered solution was concentrated and the residue was purified by column chromatography using silica gel as absorbant and hexane ethyl acetate mixture as eluant. The fractions containing clean naltrexone acetate ester-d3 were combined and concentrated to give 0.5 mg product as an oil. MS analysis gave MH+387.

Step 2: Preparation of Working Standard Solutions and Internal Standard Solution.

Working standard solutions of naltrexone were prepared by weighing naltrexone and diluting the stock solution to appropriate concentration as follows:

| Solution | |
|---|---|
| A | 0.5 ng/ml in ethyl acetate |
| B | 1 ng/ml |
| C | 2 ng/ml |
| D | 5 ng/ml |
| E | 25 ng/ml |
| F | 100 ng/ml |
| G | 125 ng/ml |

Working quality control standard solutions of naltrexone were prepared by independently weighing naltrexone and diluting the stock solution to appropriate concentration as follows:

| QC Solution | |
|---|---|
| J | 1.5 ng/ml in ethyl acetate |
| K | 70 ng/ml |

Working internal standard solution of naltrexone were prepared by preparing a stock solution of naltrexone acetate ester-d3 and diluting the stock solution to a working concentration of 10 ng/ml in ethyl acetate.

Step 3: Preparation of Calibration Samples and Quality Control Samples in Human Plasma.

Naltrexone-free human plasma aliquots of 0.1 ml were treated with 1000 ul of solution A to G to make calibration samples A to G.

Naltrexone-free human plasma aliquots of 0.1 ml were treated with 1000 ul of solution J and K to make quality control samples J and K.

Both calibration samples and quality control samples were then treated with 400 ul of the internal standard working solution.

Step 4: Conversion to Esters and Extraction.

To all prepared samples were added 100 ul of 1M aqueous sodium bicarbonate followed by 100 ul of a 10% v/v acetic anhydride in ethyl acetate. The samples were mixed and shaked at room temperature for 15 minutes. The samples were extracted with 0.5 ml ethyl acetate. Each extract was separated and concentrated. The residue of each extract was reconstituted with 100 ul of acetonitrile.

Step 5: Analysis of Reconstituted Extracts by LC/MS/MS.

A total of 9 reconstituted extracts were loaded on a Perkin Elmer autosampler that was connected to aPerkin Elmer LC pump and a PE Sciex API 365 MS. Each extract was run through an Symmetry C-18 column of 5 um at a rate of 0.3 ml/min of acetonitrile/water 50/50 mixture. The eluate was directly fed to the MS ion source. MS data were collected for 1.5 min per injection.

MS analysis was performed in MRM mode. m/z 384.0>m/z 366.2 was monitored for naltrexone acetate ester while m/z 387.0>m/z 369.2 was monitored for naltrexone acetate ester-d3. Collected data were ploted against concentration using McQuan 1.5 sofware.

Results are tabulated as follows:
Naltrexone

Internal Standard: is
Weighted (1/x*x)
Intercept=0.037
Slope=0.125
Correlation Coeff.=0.994
Use Area

| Filename | Filetype | Accuracy | Conc. | Calc. Conc. | Int. Ratio |
|---|---|---|---|---|---|
| Keto A | Standard | 95.797 | 0.500 | 0.479 | 0.079 |
| Keto B | Standard | 99.105 | 1.000 | 0.991 | 0.160 |
| Keto C | Standard | 113.326 | 2.000 | 2.267 | 0.319 |
| Keto D | Standard | 114.829 | 5.000 | 5.741 | 0.752 |
| Keto E | Standard | 96.193 | 25.000 | 24.048 | 3.032 |
| Keto F | Standard | 89.559 | 100.000 | 89.559 | 11.193 |
| Keto G | Standard | 92.888 | 125.000 | 116.110 | 14.500 |
| Keto J | QC | 87.039 | 1.500 | 1.306 | 0.200 |
| Keto K | QC | 126.069 | 70.000 | 88.248 | 11.029 |

REFERENCES

U.S. patent documents

| | | |
|---|---|---|
| 5,559,038 | Sep. 24, 1996 | J. Fred Kolhouse |
| 6,358,996 | Mar. 19, 2002 | Michael S. Alexander |

Other References

Mark M. Kushnir et al, "Comparison of four derivatizing reagents for 6-acetylmorphine GC-MS analysis", Journal of Analytical Toxicology, July/August 1999, page 262-269, vol. 23.

Michael L. Smith et al, "Forensic drug testing for opiates. VI. Urine testing for hydromorphone, hydrocodone, oxymorphone, and oxycodone with commercial opiate immunoassay and GC-MS", Journal of Analytical Toxicology, January/February 1995, page 18-26, vol. 19.

J. G. Guillot et al, "Determination of heroin, 6-acetylmorphine, and morphine in biological fluids using their propionyl derivatives with ion trap GC-MS", Journal of Analytical Toxicology, March/April 1997, page 127-133, vol. 21.

We claim:

1. A method of quantification of alcohol(s) in a sample comprising the steps of:
   a) synthesizing a stable isotope labeled ester internal standard of said alcohol, wherein the ester is selected from a group consisting of $R_1OCOR_4$, $R_1CH_2OCOR_4$, $R_1R_2CHOCOR_4$, and $R_1R_2R_3OCOR_4$ where $R_1$, $R_2$, and $R_3$ are alkyl, aryl, and heteroatom containing cyclic or non-cyclic groups, and $R_4$ is a stable isotope labeled alkyl or aryl group, by reacting an authentic sample of said alcohol with a stable isotope labeled reagent;
   b) combining a known amount of the synthesized stable isotope labeled ester internal standard of said alcohol with said sample comprising said alcohol;
   c) contacting said combined sample and the internal standard with an acid anhydride or an acid chloride to quantitatively convert said alcohol in said sample into an ester of identical structure as that of said stable isotope labeled ester internal standard except for the stable isotope atoms, wherein there is no conversion of said stable isotope labeled ester internal standard to its corresponding non-labeled ester compound;
   d) extracting said ester and said stable isotope labeled ester internal standard from said combined sample;
   e) quantifying said ester by isotope dilution mass spectrometric method using said stable isotope labeled ester internal standard; and, f) calculating the amount of said alcohol in said sample from the amount of said ester.

2. The method of claim 1 wherein said alcohol has molecular mass less than 1000 atomic unit and is selected from the group consisting of $R_1OH$, $R_1CH_2OH$, $R_1R_2CHOH$, $R_1R_2R_3COH$, wherein $R_1$, $R_2$, and $R_3$ are alkyl, aryl, and heteroatom containing cyclic or non-cyclic groups.

3. The method of claim 1 wherein said labeled group $R_4$ is selected from a group consisting of $CD_3$, $CD_2CD_3$, and $C_6D_5$, formed by reacting said alcohol with labeled acid anhydride selected from a group comprising labeled acetic acid anhydride, labeled propionic acid anhydride, and labeled benzoic acid anhydride or labeled acid chloride selected from a group comprising labeled acetyl chloride, labeled propionyl chloride, and labeled benzoyl chloride.

4. The method of claim 1 wherein said extraction step d) can be any appropriate separating methods such as solid phase extraction, liquid-liquid extraction or solid supported liquid-liquid extraction.

5. The method of claim 1 wherein said acid anhydride is selected from a group consisting of acetic acid anhydride, propionic acid anhydride, and benzoic acid anhydride and said acid chloride is selected from a group consisting of acetyl chloride, propionyl chloride, and benzoyl chloride.

6. The method of claim 1 wherein said sample contains either a singularity or a plurality of alcohols.

7. The method of claim 6 wherein said plurality of alcohols can be converted to multiple esters using a single acid anhydride or a single acid chloride.

8. The method of claim 6 wherein a plurality of labeled ester internal standards can be synthesized from said plurality of alcohols using a single labeled acid anhydride or a single labeled acid chloride.

9. The method of claim 1 wherein said converting step c) is performed in an aqueous environment.

10. A method of quantification of alcohol(s) in a sample comprising the steps of:
a) synthesizing a stable isotope labeled carbamate internal standard of said alcohol, wherein the carbamate is selected from a group consisting of $R_1OCONR_4$, $R_1CH_2OCNR_4$, $R_1R_2CHOCONR_4$, and $R_1R_2R_3OCNR_4$, where $R_1$, $R_2$, and $R_3$ are alkyl, aryl, and heteroatom containing cyclic or non-cyclic groups, and $R_4$ is a stable isotope labeled alkyl or aryl group, by reacting an authentic sample of said alcohol with a stable isotope labeled reagent;
b) combining a known amount of the synthesized stable isotope labeled carbamate internal standard with said sample comprising said alcohol;
c) contacting said combined sample and the stable isotope labeled carbamate internal standard with an isocyanate to quantitatively convert said alcohol in said sample into a carbamate of identical structure as that of said stable isotope labeled carbamate internal standard except for the stable isotope atoms, wherein there is no conversion of said stable isotope labeled carbamate internal standard to its corresponding non-labeled carbamate compound;
d) extracting said carbamate and said stable isotope labeled carbamate internal standard from said combined sample;
e) quantifying said carbamate by isotope dilution mass spectrometric method using said stable isotope labeled carbamate internal standard; and
f) calculating the amount of said alcohol in said sample from the amount of said carbamate.

11. The method of claim 10 wherein said alcohol is an alcohol having the following formula $R_1OH$, $R_1CH_2OH$, $R_1R_2CHOH$, $R_1R_2R_3COH$, wherein $R_1$, $R_2$, and $R_3$ are alkyl, aryl, and heteroatom containing cyclic or non-cyclic groups.

12. The method of claim 10 wherein said labeled group $R_4$ is selected from a group consisting of $CD_3$, $CD_2CD_3$, and $C_6D_5$, formed by reacting said alcohol with a labeled isocyanate selected from a group comprising labeled methyl isocyanate, labeled ethyl isocyanate, and labeled phenyl isocyanate.

13. The method of claim 10 wherein said extraction step d) can be any appropriate separating methods such as solid phase extraction, liquid-liquid extraction or solid supported liquid-liquid extraction.

14. The method of claim 10 wherein said isocyanate is selected from a group consisting of methyl isocyanate, ethyl isocyanate and phenyl isocyanate.

15. The method of claim 10 wherein said sample contains either a singularity or a plurality of alcohols.

16. The method of claim 15 wherein said multiple alcohols can be converted to said carbamates using a single isocyanate.

17. The method of claim 15 wherein said multiple labeled carbamate internal standards can be synthesized from said alcohols using a single labeled isocyanate.

18. The method of claim 10 wherein said converting step c) is performed in an aqueous environment.

\* \* \* \* \*